(12) United States Patent
Peer

(10) Patent No.: US 6,238,384 B1
(45) Date of Patent: May 29, 2001

(54) INSTRUMENT FOR COMPENSATING FOR HAND TREMOR DURING THE MANIPULATION OF FINE STRUCTURES

(76) Inventor: Ferdinand Peer, Kunhardtstrasse 3, 20249 Hamburg (DE)

( * ) Notice: Subject to any disclaimer, the term of this patent is extended or adjusted under 35 U.S.C. 154(b) by 0 days.

(21) Appl. No.: 09/142,426
(22) PCT Filed: Jan. 7, 1998
(86) PCT No.: PCT/DE98/00043
  § 371 Date: Dec. 28, 1998
  § 102(e) Date: Dec. 28, 1998
(87) PCT Pub. No.: WO98/30165
  PCT Pub. Date: Jul. 16, 1998

(30) Foreign Application Priority Data

Jan. 8, 1997 (DE) .............................................. 197 00 402

(51) Int. Cl.[7] .................................................. A61B 17/00
(52) U.S. Cl. .............................. 606/1; 340/318; 340/317; 128/898
(58) Field of Search ....................... 606/1, 130, 139–144, 606/167; 414/1–5; 382/98; 396/52–55; 128/897, 898; 250/559.29, 559.33; 248/562, 564

(56) References Cited

U.S. PATENT DOCUMENTS

| 4,689,449 | * | 8/1987 | Rosen . | |
|---|---|---|---|---|
| 4,800,802 | | 1/1989 | Rebman | 92/61 |
| 5,209,326 | | 5/1993 | Harper | 188/378 |
| 5,312,434 | | 5/1994 | Crainich | 606/207 |
| 5,571,137 | | 11/1996 | Marlow et al. | 606/207 |
| 5,634,142 | * | 5/1997 | Imafuji et al. . | |
| 5,635,725 | * | 6/1997 | Cooper . | |
| 5,762,458 | * | 6/1998 | Wang et al. . | |
| 5,822,813 | * | 10/1998 | Powell . | |

FOREIGN PATENT DOCUMENTS 0 425 352 A1   5/1991   (EP) .
0 715 092 A2   6/1996   (EP) .

* cited by examiner

Primary Examiner—John Mulcahy
Assistant Examiner—Ahmed Farah
(74) Attorney, Agent, or Firm—Klaas, Law, O'Meara & Malkin, P.C.; Michael A. Goodwin, Esq.

(57) ABSTRACT

An instrument for the manipulation of fine structures, said instrument detecting hand tremor and compensating for this hand tremor by effecting counter-movements of the working tip. The main area of application will probably lie in the field of microsurgery, since the operations performed in said field can be made difficult by the hand tremor of the operating surgeon. Here, the tremor is detected by movement sensors, by repeated analysis of the position of the handheld part (1) of the instrument, or by deriving electromyographic signals from the forearm of the operator. Intentional and unintentional movements are differentiated from one another on the basis of one or more criteria, such as movement amplitude, speed, frequency and direction. To compensate for undesired movements, signals are sent to an arrangement of actuators (3) which cause deflections of the movable part (4) of the instrument, which deflections at the tip of the instrument compensate for the hand tremor. When the instrument is used as a needle holder in surgery, the actuators (3) can also be controlled by push button in such a way that, by oscillations, they facilitate the penetration of the suture needle into the area being worked on.

22 Claims, 2 Drawing Sheets

INSTRUMENT FOR COMPENSATING FOR HAND TREMOR DURING THE MANIPULATION OF FINE STRUCTURES

DESCRIPTION

Manual work on fine structures is made much more difficult by the contraction of antagonistic muscles occurring involuntarily, and in largely rhythmic succession, and referred to as tremor. This is noticeable particularly in microsurgery when suturing fine nerves or vessels, prolongs the duration of the operation and reduces the quality of the result.

However, in order to be able to perform filigree work, use is made, for example, of supports for the hands, or micromanipulators, which convert relatively rough movements into fine deflections.

The object of the invention is to make available a handheld instrument for the manual manipulation of fine structures, in which undesired movements, for example tremor, have no effect, or at least less effect, on the manipulation.

The invention is based on the concept of evaluating the undesired movements of handheld instruments and of deflecting, by means of actuators, the working tip of the instrument (in surgical applications this would be, for example, a needle holder) in order to provide compensation, so that the hand tremor cannot be observed at the tip.

Since the physiological tremor takes place in a range of between about 5 and 15 strokes/second, it can be differentiated from slower voluntary movements, for example by frequency-selective filtering.

Movement Detection

According to the invention, one or more devices can be provided for detecting movements on the part of the user, in particular for detecting movements of the instrument caused by the user, for example active or passive measurement transducers, by means of which undesired movements on the part of the user, or movements of the instrument caused by the user, can be detected. The output signals from these devices are used, if appropriate after suitable evaluation and processing, to trigger actuators of the instrument for the purpose of compensating for the undesired movements.

To detect the movement of the instrument, a number of possibilities can be selected in principle, and these can be combined with one another:

1. Acceleration and angular velocity sensors are arranged on one or more sections of the instrument, which sensors supply a mechanical or electrical signal correlated with the movement of the instrument.

The function of the sensors can be based on purely mechanical, electromagnetic, capacitive, piezoelectric or piezoresistive principles. The sensors have to detect the movement with sufficient sensitivity and accuracy. In this connection, it is conceivable to use sensors which have their maximum sensitivity in the frequency range in which the undesired movements take place and thereby deliver an output signal correlated with the tremor. The sensors can be arranged in such a way that they can detect both translational movements and rotational movements of the instrument.

2. According to the invention, one or more devices can be provided for repetitive or continuous detection of the position of certain sections of the instrument in one, two or three dimensions, in particular of a handheld section and/or a section of the instrument which is movable in relation to the handheld section. By repetitive or continuous detection of the position and orientation of certain sections of the instrument, their movement can be followed. The detection can take place in one, two or three dimensions. This can be done by wireless means via a transmitter/receiver system on the instrument and at reference points which are located at fixed positions in space or on the area being worked on.

It is also possible, particularly for use in microsurgery, to follow the movement of the section of the instrument shown in the operating microscope. The microscope image is delivered to an image-recording unit which determines the positions, in the image, of certain features or optical markings on the instrument and calculates the movement on the basis of the consecutive position data. To do this, tracking procedures can also be used.

If, in addition, the movement of the tissue being worked on is also detected, this movement likewise being shown under the operating microscope, the movement of this tissue caused, for example, by the tremor on the part of the patient can be included in the compensation process.

3. With surface electrodes arranged on the skin of the person operating the instrument, the action potentials of the underlying muscle can be recorded (so-called electromyography). If a control system recognizes the movement which the corresponding muscle causes on innervation—for example through the ability to adapt—it is possible, by combining the electrode signals, to draw conclusions regarding the deflection the instrument is expected to make. In this method, the actual use of the instrument would be preceded by a "learning phase" in which the signal processing unit correlates the electromyographic signals with results of other movement-recording methods, and thus adapts to individual features of the operator and to the positioning of the reference electrodes.

Signal Processing

If the movement detection has not already supplied a signal which corresponds to the movement attributed to the tremor and is thus suitable for directly triggering the actuators, the signal is processed.

In general, it will first be necessary to amplify the sensor signal. This is followed by analysis which differentiates between intentional and unintentional movements on the basis of criteria such as frequency, amplitude, speed and direction. The criteria can be predefined, adjusted, or adapted automatically. On the basis of the data, a signal is obtained with which the actuators are triggered so that said actuators execute, at the working tip of the instrument, relative movements for compensating for the undesired deflections of the handheld section.

Actuators

The actuators can be both purely mechanical arrangements and also electrical controls which are based, for example, on electromagnetic, capacitive or piezoelectric principles. The actuators execute relative movements between the handheld section and the movable section of the instrument. They must be able to execute the desired movements with sufficient speed, power and precision. The actuators can be arranged in such a way that they can effect both translational movements and rotational movements. For certain requirements, it may be desirable that the actuators can also temporarily bring about a rigid connection between the handheld section and the movable section. The working tip of the instrument can be mounted in a fixed manner or can be designed to be exchangeable. Actions, such as the opening and closing of grippers or forceps, which must necessarily be done from the handheld section of the instrument, can be triggered via a flexible power transmission, for example a flexible push rod, which does not impede the actuators, or via electrically operated adjustment members on the moved section.

Additional Functions

It may be useful, especially for use in microsurgery, to trigger the actuators already present in the instrument by means of a push button in such a way that they cause the working tip of the instrument to oscillate at frequencies in the sonic or ultrasonic range, and, for example, when used as a needle holder, facilitate the penetration of the suture needle into tissue, as a result of the rapid micro-movements.

ILLUSTRATIVE EMBODIMENT

An illustrative embodiment of the invention is explained in greater detail below, with reference to the attached drawings.

Figure 1:
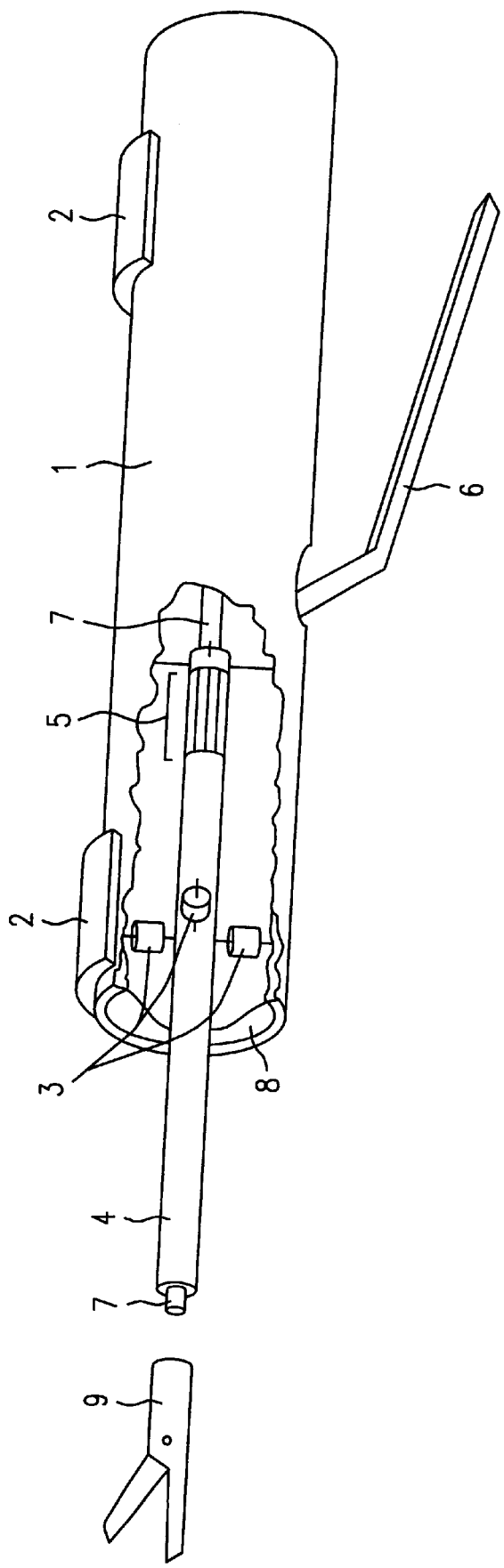
FIG. 1 is a partial cutaway perspective view of a medical instrument.

In FIG. 1, reference (1) designates the handheld section of a medical instrument. Groups of acceleration meters and angular velocity sensors (2) sit on this section. A movable section (4) is connected to the handheld section (1) via a flexible connection (5), and on this movable section (4) the working tip is, for example, a needle holder. The movable section can be moved relative to the handheld section (1) by the arrangement of piezoelectric actuators (3). The actuators (3) are arranged in such a way that they can bring about deflections in all directions transverse to the main axis of the instrument.

A control unit fed by a battery is located in the handheld section (1), said control unit amplifying the data supplied by the sensors (2), continuously analyzing this data and comparing it.

On the basis of adaptable criteria such as acceleration, frequency, direction and amplitude of the movement, the control unit differentiates between desired movements and the hand tremor of the operator.

To compensate for the hand tremor, the arrangement of the actuators (3) is triggered in combination in such a way that these effect relative movements of the movable part (4) which are adapted in direction, speed and amplitude, and the undesired movements of the hand grip (1) cannot be observed at the working tip of the instrument holder (4). For opening and closing needle holders, forceps or scissors, use is made of a push rod (7) which flexibly designed in the area of the flexible connection (5) and which extends through the inside of the movable section (4). The push rod is operated via a lever (6). A flexible membrane (8) on the end face of the handheld section (1) is used to seal off the mechanism.

Figure 2:
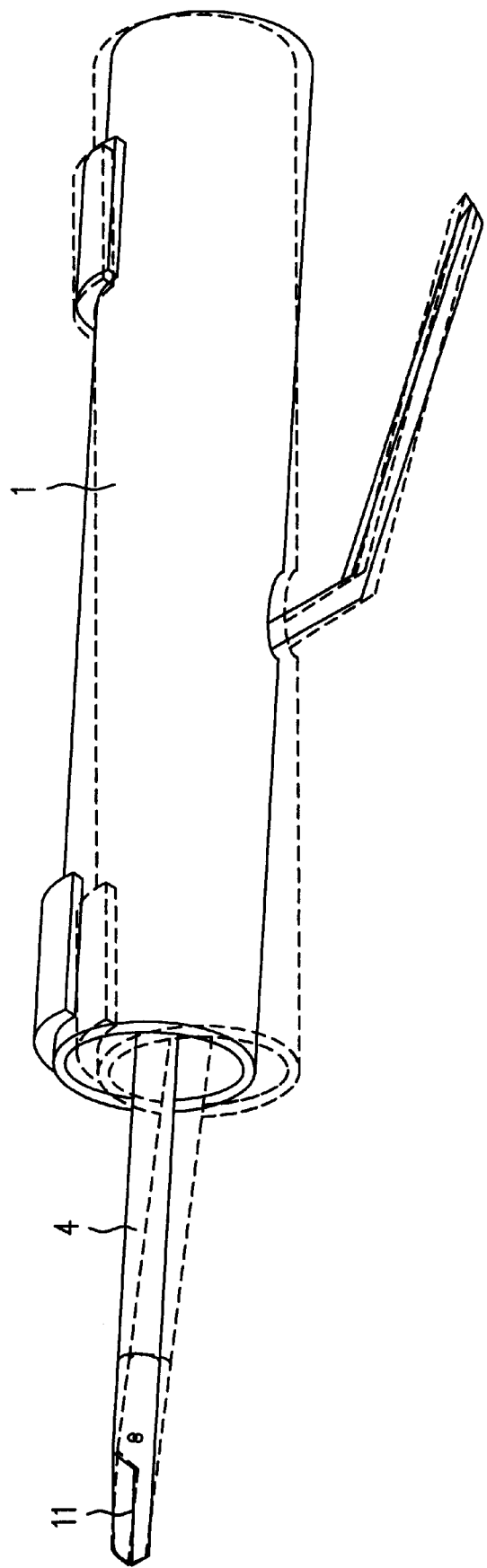
FIG. 2 is a perspective view of the medical instrument of FIG. 1 illustrating, in dashed lines, an example of the function of the instrument.

The function of the instrument is additionally shown in FIG. 2.

A rapid and unintentional pitching movement of the handheld section (4), caused by tremor, would lead to an undesired deflection of the working tip (11) of the instrument. In order to prevent this, the actuators (3) are triggered for compensation so that the movable section (4) is moved in the opposite direction, and the working tip (11) remains at rest.

What is claimed is:

1. Instrument for the manual working of fine structures, comprising:
    (a) a handheld section,
    (b) a section which is movable in relation to the handheld section,
    (c) actuators,
and where
    (d) the actuators are designed to effect relative movements between the handheld section and the movable section, which relative movements compensate at least partially for movements of the handheld section.

2. Instrument according to claim 1, characterized in that one or more sensors are arranged on the handheld section, said sensors detecting the movement of the handheld section, and said sensors being capable of generating an output signal used to trigger the actuators.

3. Instrument according to claim 2, characterized in that at least one sensor detects the acceleration.

4. Instrument according to claim 1, characterized in that one or more sensors are arranged on the movable section, said sensors detecting the movement of the movable section, and their output signal being used to trigger the actuators.

5. Instrument according to claim 1, characterized in that one or more sensors are arranged on the handheld section or on the movable section or between the handheld section and the movable section, said sensors detecting the relative movement between the handheld section and the movable section, and said sensors being capable of generating an output signal used to trigger the actuators.

6. Instrument according to claim 1, characterized in that one or more sensors are provided for repetitive or continuous detection of the position of the handheld section in one, two or three dimensions.

7. Instrument according to claim 6, characterized in that the position of the instrument is detected optically via the ray path of an operating microscope.

8. Instrument according to claim 1, characterized in that one or more sensors are provided for repetitive or continuous detection of the position of the movable section in one, two or three dimensions.

9. Instrument according to claim 1, characterized in that a control or regulating unit triggers the actuators on the basis of the data from the sensors for position detection or movement detection.

10. Instrument according claim 1, characterized in that a control or regulating unit triggers the actuators on the basis of a repetitive or continuous position detection.

11. Instrument according to claim 1, characterized in that electromyographically detected potentials are used to trigger the actuators.

12. Instrument according to claim 1, characterized in that when movements of the handheld section or movable section occur, the compensation movements take place in a predetermined or adjustable or automatically adapting frequency range.

13. Instrument according to claim 1, characterized in that when movements of the handheld section or movable section occur, the compensation movements take place in a predetermined or adjustable or automatically adapting amplitude range.

14. Instrument according to claim 1, characterized in that the actuators are capable of being triggered in such a way that a rigid connection is obtained between the handheld section and the movable section.

15. Instrument according to claim 1, characterized in that the actuators are capable of being triggered in such a way that the actuators can generate oscillations of the movable section.

16. A method of performing work, comprising:

providing an instrument having:
- (a) a first section;
- (b) a second section which is moveable relative to said first section;
- (c) at least one actuator operatively connected between said first section and said second section;

performing work with said second section by imparting movement to said first section; and preventing at least a portion of said movement from being transmitted to said second section by activating said at least one actuator;

wherein said imparting movement to said first section comprises imparting at least a first type and a second type of movement to said first section;

wherein said first type of movement comprises involuntary muscle movements;

wherein said second type of movement comprises voluntary muscle movements; and wherein said preventing at least a portion of said movement from being transmitted comprises preventing said first type of movement from being transmitted and allowing said second type of movement to be transmitted.

17. The method of claim 16 and further comprising:

providing at least one sensor on said first section;

detecting said at least a portion of said movement with said at least one sensor; and wherein said preventing at least a portion of said movement includes outputting a signal from said at least one sensor.

18. The method of claim 17 wherein said detecting said at least a portion of said movement with said at least one sensor comprises sensing acceleration.

19. The method of claim 16 and further comprising:

optically detecting the position of said instrument.

20. The method of claim 19 and further comprising:

providing a microscope; and said optically detecting the position of said instrument is accomplished with said microscope.

21. The method of claim 19 wherein said preventing at least a portion of said movement from being transmitted is based on said optically detecting the position of said instrument.

22. The method of claim 16 and further comprising:

electromyographically detecting potentials; and wherein said preventing at least a portion of said movement from being transmitted to said second section by activating said at least one actuator is accomplished based upon said potentials.

* * * * *